(12) United States Patent
Bensley-Bromilow et al.

(10) Patent No.: US 9,227,230 B2
(45) Date of Patent: Jan. 5, 2016

(54) METHOD FOR OBTAINING SUBSTANTIALLY PURE HYBRID CEREAL SEED AND MACHINE FOR USE THEREOF

(75) Inventors: John Charles Battleaxe Bensley-Bromilow, Basel (CH); Robert Fitzpatrick Bruns, Berthoud, CO (US); Barry Andrew Martin, Basel (CH); Karsten Neuffer, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 170 days.

(21) Appl. No.: 13/824,990

(22) PCT Filed: Sep. 16, 2011

(86) PCT No.: PCT/EP2011/066136
§ 371 (c)(1),
(2), (4) Date: Mar. 18, 2013

(87) PCT Pub. No.: WO2012/038350
PCT Pub. Date: Mar. 29, 2012

(65) Prior Publication Data
US 2013/0167496 A1    Jul. 4, 2013

(30) Foreign Application Priority Data

Sep. 20, 2010 (GB) .................................. 1015791.5

(51) Int. Cl.
*B07C 5/342* (2006.01)
*A01H 1/04* (2006.01)
*G01N 21/3563* (2014.01)
*G01N 21/359* (2014.01)
*A01D 45/30* (2006.01)

(52) U.S. Cl.
CPC .............. *B07C 5/3425* (2013.01); *A01D 45/30* (2013.01); *A01H 1/04* (2013.01); *B07C 5/342* (2013.01); *G01N 21/359* (2013.01); *G01N 21/3563* (2013.01)

(58) Field of Classification Search
CPC .................. B07C 5/342; G01N 21/00; G01N 2021/2592; A01D 41/12; A01D 41/00
See application file for complete search history.

(56) References Cited

U.S. PATENT DOCUMENTS

| | | | | |
|---|---|---|---|---|
| 6,100,526 A | * | 8/2000 | Mayes | ....................... 250/339.11 |
| 6,646,264 B1 | * | 11/2003 | Modiano et al. | .......... 250/339.07 |
| 7,274,457 B2 | * | 9/2007 | Janni | ............................. 356/432 |

FOREIGN PATENT DOCUMENTS

| | | | |
|---|---|---|---|
| CA | 2280364 | | 2/2001 |
| WO | 92/01366 | | 2/1992 |
| WO | 03/004179 | | 1/2003 |
| WO | WO 03/004179 | * | 1/2003 |

OTHER PUBLICATIONS

International Search Report, International Application No. PCT/EP2011/066136, completion date: Dec. 6, 2011.
Perez-Prat E et al: "Hybrid seed production and the challenge of propagating male-sterile plants", Trends in Plant Science, Elsevier Science, Oxford, GB, vol. 7, No. 5, May 1, 2002, pp. 199-203.

* cited by examiner

*Primary Examiner* — Susan McCormick Ewoldt
(74) *Attorney, Agent, or Firm* — Dale Skalla

(57) ABSTRACT

The present invention relates to a method for obtaining substantially pure hybrid cereal seed and a machine for use thereof. In particular the invention describes a method for separating hybrid barley seed from a mixed population of inbred barley seed and hybrid barley seed on the basis of a difference which is detectable via the use of near infrared light.

5 Claims, No Drawings

METHOD FOR OBTAINING SUBSTANTIALLY PURE HYBRID CEREAL SEED AND MACHINE FOR USE THEREOF

This application is a 371 of International Application No. PCT/EP2011/066136 filed Sep. 16, 2011, which claims priority to GB 1015791.5 filed Sep. 20, 2010, the contents of which are incorporated herein by reference.

The present invention relates to a method for generating a population of $F_1$ hybrid seed and inbred seed and then sorting said seed on the basis of a difference between said $F_1$ hybrid and said inbred seed. In particular this method is applicable to the sorting of cereal seeds, in particular wheat seed, barley seed, triticale seed, and rye seed.

Cereal crops are cultivated in most countries around the world and are a rich source of protein, carbohydrates, minerals, vitamins, oils and fats. The term cereal typically embraces grasses from the monocot families of plants known as Poaceae or Gramineae. Of particular interest are the cereal crops wheat and barley.

Wheat is a key global food crop; it is a leading source of vegetable protein in food and is the most internationally traded food crop. Wheat grains are used in the generation of various foodstuffs including: breads; biscuits; pasta; breakfast cereals; animal feed and can be fermented for use in brewing or used in the generation of biofuels. In addition, the other parts of the wheat plant can be used as construction materials such as thatching. Surprisingly global wheat production is increasing at less than 1% per year whereas some sources state demand is increasing at 1.5% per year. With the world's population increasing, there remains a need to generate even more efficient methods for maximising the output from the world's increasingly valuable and precious agricultural land.

Barley is a cereal grain derived from *Hordeum vulgare*. Reports have stated that it is grown in over 100 countries worldwide and its grain is primarily of use as a foodstuff. More specifically, barley is commonly used in animal feed, however, it is also used for malting to generate a key flavour ingredient in beer and whisky. Barley is also used in other foodstuffs and in the production of other alcoholic and non alcoholic beverages.

The benefits of high yielding hybrid plants have long since been recognised. Hybrid varieties will often exhibit an extremely uniform phenotype relative to their inbred parents. The hybrid benefits from the combined traits of the parents leading to enhanced disease resistance and vigour which in turn can translate into increased yield. Hybrids also afford a simple breeding opportunity to combine characteristics or traits that may be difficult to combine in other ways and usually give a greater return unit for growth factors such as water and fertilizer.

$F_1$ Hybrids are produced via the fertilisation of a male sterile, female plant with pollen from a male donor plant. Therefore, one critical aspect of hybrid production is ensuring that the female plant is prevented from self-pollinating whilst remaining fertile. Various methods and techniques are known in the art for obtaining the male sterility of the female parent. Examples include: mechanical removal of the male pollen producing part of the plant such as "de-tasseling" as performed in maize.

The use of cytoplasmic male sterility (CMS) for commercial hybrid production requires a stable male-sterile cytoplasm and a source of pollen. The cytoplasmic-genetic system of male sterility requires the existence of three types of line for hybrid production, the A line (cytoplasmic male-sterile), B line (male-fertile maintainer) and R line (male fertile with restorer genes). Crosses produced with this system involve maintenance and production of three lines, an A and a B line of one inbred crossed to increase the seed of the female parent in the A line state to be used in the final hybrid production and male-fertile R line containing the restoration gene(s) used as the male component of the final hybrid production.

Hybrid seed can also be produced through the use of chemicals that inhibit viable pollen formation. These chemicals, called gametocides, are used to impart transitory male-sterility.

Hybrids can further be generated via the use of molecular biology techniques. In general, the female parent can be engineered such that pollen production is disabled to achieve the male sterility. Such techniques have also been widely reported and are well known to the skilled person. A more recent refinement of such techniques involves a chemical male sterility system based upon the conversion of the inactive D-enantiomer (D-glufosinate) of the herbicide glufosinate to the phytotoxic L-enantiomer (L-glufosinate), which conversion is localised to the anthers. The conversion of the non-phytotoxic D-glufosinate to the phytotoxic L-glufosinate, results in the highly localised destruction of the anther, thereby rendering the plant male sterile. This conversion is effected via an activating enzyme (a modified form of a D-amino acid oxidase) which is specifically expressed in the anthers. This system is described further in WO2005/005641.

A major shortcoming of traditional hybrid seed production systems is the need to plant separate rows, strips or blocks of the male and female parent lines. With respect to wheat hybrid production for example, this is sometimes referred to as the bay-planting system. One characterising feature of the bay-planting system is that the male and female plants are separated in different bays. The male bay contains the male pollinator plants and this is totally separate from the female bay which contains the male sterile females. The bays are separated to such a degree that the entire female bay can be harvested safe in the knowledge that it will not contain any male inbred seed as the males are present in a separate bay. An analogous system for barley hybrid production exists where the plants are planted in strips of males and females. Here low efficiency pollination is an especially acute problem in crop species, such as wheat and barley, that release small amounts of pollen which does not travel far on the wind and only remains viable for a very short period of time. In such crops, as much as two/thirds of the hybrid-producing field needs to be dedicated to male pollen-donor plants and then hybrid seed production therefore becomes uneconomic.

In order to achieve more economic seed production in wheat and barley crops it would be necessary to move male and female plants closer together for more efficient pollen transfer; most efficiently by inter-planting males and females within centimetres of each other in the same rows. However, in such a system it would be impractical to harvest only the seed from the (male-sterile) female parents.

Furthermore, whilst barley hybrids can be generated via the inter-planting system, there is limited practical scope to do this since the harvested seed contains both the hybrid and the inbred and the tolerance for inbred "contamination" within the harvested seed is relatively low. One problem with the inter-planting technique relates to the overall hybrid production efficiency since the number of males used within the inter-planting technique can only be small to adhere to the strict limits of a low percentage of inbred seed being present within the overall harvest of hybrid seed obtained via this technique. The low number of males used means that, taking account of the low pollination efficiency as mentioned above, a section of the female plants will not be pollinated and thus will not produce any grain at all. This has an impact on the overall field yield and increasing the number of males to increase pollination efficiency will not overcome this since that will increase the number of inbred seed in the overall yield taking the inbred percentage obtained within the overall harvest outside of the tolerated limits. This represents a significant barrier which affects the efficiency of the inter-planting hybrid system. Furthermore, there is a need for the provision of a system whereby the hybrid seed yield can be easily checked to ensure that the percentage of inbred seed is within the approved limits. In addition, there is a need for the provision of a system which can ensure that the in-bred seed present within the harvested hybrid seed meets such limits by, wherever necessary, removing any excess inbred seed to meet the official requirements.

The generation of hybrid cereals such as wheat and barley in an economically feasible way remains an issue. As described above, the separate bay-planting/strip planting approach is a high cost approach and the lower cost inter-planting system remains impractical with marginally low hybrid seed yield.

Taking into account these problems, a need exists to develop methods for increasing the yield of wheat and barley and to provide a mechanism whereby the wheat and barley grain can be harvested in a commercially acceptable manner. The present invention is directed towards solving the various problems that exist in the present methods for the production of hybrid wheat and hybrid barley, in particular hybrid barley. Moreover, with the rise in demand for food by the increasing world population, there remains the need for more efficient processes for producing high quality crops such as hybrid barley and wheat and maximising the use of the limited agricultural land available by, inter alia, reducing waste due to non-pollination of female plants in hybrid production.

According to the present invention there is provided a method for separating inbred seed from a mixed population of inbred and hybrid seed the method comprising: (a) providing a mixed population of inbred and hybrid seed; and (b) subjecting said seed to a device which separates said mixed population into (i) a population of substantially inbred seed and (ii) a population of substantially hybrid seed characterized in that said seed is cereal seed and said device separates said inbred seed on the basis of a difference which is detectable via the use of near infrared light. The method according to the invention can also be used to separate the hybrid seed from the inbred seed. The net effect of the method of the invention is the provision of a set of inbred seed and a set of hybrid seed which have been separated from a mixed population thereof. The device will typically comprise a means for sampling each seed within the population which will typically involve separating the seeds in such a manner that each individual seed can be sampled. Said sampling will involve determining the reflective and/or absorbance characteristics of each seed using near infrared light. For example, the seed can be illuminated by light of a pre-defined spectrum and the spectral features of the reflected light are measured. For detection via transmission, the detector is positioned such that it measures the light which is transmitted through the seed, and thus measures the spectral features of the light which is transmitted through the seed. Once this data is obtained the device will recognize the seed as being inbred or hybrid based on the measurements taken from the seed when compared with the control standards as recognized by the device. Typically this operation will be performed via a computerised comparison of the data received from the seed sample with pre-programmed standards such that the seed can be identified as inbred or hybrid based. Once analysed and identified as either hybrid or inbred the device will provide a means for separating the seed into a collection area which contains the seeds which have been subjected to the same analysis and yielded the same results. Via the operation of this device, the mixed population of seeds is consequently separated into the component inbred and hybrid parts. Examples of devices which can be used in accordance with the methods of the present invention include those described in U.S. Pat. Nos. 7,202,434 and 7,417,203.

The difference between the hybrid and inbred seed according to the methods and devices of the invention in this specification may also be detected via the use of terahertz radiation imaging, electromagnetic radiation; sonic waves; ultraviolet light; infrared light, fluorescent light; ultrasonic waves; microwaves; nuclear magnetic resonance alone or in combination. Such detection methods may also be advantageously combined with near infrared.

The hybrid and inbred seed are advantageously differentiated according to the invention without the need to destroy or adversely affect the seed. Moreover the use of near infrared provides for a mechanism to differentiate between the hybrid and inbred seed without the need to sort based on protein content, oil content or colour as which are already generally known as means for differentiating seeds generally in the prior art. The method of the present invention therefore provides a means to differentiate between hybrid and inbred seed based upon features of the seed which are not typically/significantly affected by the growing environment.

The present invention still further provides a method according to any of the previous claims wherein said device comprises: (a) a means for sampling each seed within the mixed population; and (b) a means for obtaining the near infrared spectral data for each seed; and (c) a means for identifying each seed as inbred or hybrid seed on the basis of said spectral data; and (d) a means for separating each seed based on said data; and (e) a means for collecting the thus separated seed. The seed can be identified in accordance with this method via a comparison of the spectral data received for each sample with the spectral data for a control sample of a hybrid and an inbred.

The present invention still further provides a method as described above wherein said device separates the seed such that the resulting population of separated substantially hybrid seed comprises no more than about 5% inbred seed. The method of the invention can be utilised to ensure that the amount of inbred seed present within the hybrid seed collected for subsequent planting is within any approved limit via separation of any excess. For example, if the approved limit of inbred seed within the hybrid seed population generated for subsequent planting is 5%, the method of the invention can be employed to ensure the seed selected for subsequent planting contains no more than 5% inbred seed. Preferably the method of the invention is employed to separate out substantially all of the inbred seed, however, the method can still be operated to ensure that seed selected for subsequent planting conforms to any regulations relating to the amount of inbred seed permitted to be present in the hybrid population. In still further embodiments of the invention the method can be employed to ensure the seed selected for subsequent planting contains not more than a percentage of inbred seed selected from 1%, 2%, 3%, 4%, 5%, 6%, 7%, 8%, 9%, 10%, 11%, 12%, 13%, 14%, 15% and greater than 15%. In a particular embodiment of the invention, the method is employed on barley seed to ensure the seed selected for subsequent planting contains no more than 10% inbred seed. In a still further embodiment of the invention, the method is employed on triticale seed to ensure the seed selected for subsequent planting contains no more than 5% inbred seed.

The present invention still further provides a method as described above wherein said cereal seed is barley or wheat. In a particular embodiment of the invention the methods and machines as described in this specification are utilised for the sorting of barley seed.

The present invention still further provides a method as described above wherein said device utilises an algorithm to differentiate the near infrared spectral data obtained of said inbred and said hybrid seed which then allows the seed to be sorted on the basis of said spectral data. Prior to performing the methods of the present invention control seed can be tested to ascertain the spectral data, reflectance and/or transmission data of a selection of hybrid and inbred seeds. Once this data has been generated it can be utilised to generate an algorithm for use to discriminate between the seeds. This can then be employed in the device which, as described above, contains the means for testing each of the seeds in the general population and then on the basis of the results compared with the standards, selecting the seeds which apply to the relevant category of inbred or hybrid and separating accordingly. The skilled person is capable of generating an appropriate algorithm for use in the device described in this specification based on an identification of the spectral data of the seeds to be sorted.

The present invention still further provides a method according to any one of the previous claims wherein said difference is a genotypic difference.

The present invention still further provides a method according to any one of the previous claims wherein said difference relates to an amount of a compound selected from: glucose; xylose; mannose; galactose; arabinose; or a combination thereof, in the seed.

In a still further aspect of the present invention there is provided a method of obtaining substantially pure $F_1$ hybrid seed and substantially pure inbred seed said method comprising: (a) Inter-planting a population of parent plants within a field wherein said population contains male and female parents, wherein said female is at least partially male sterile; and (b) Providing for self-fertilisation of said male and cross-fertilisation of said female; and (c) Harvesting the resulting fertilized seed; and (d) Separating said seed on the basis of a difference between said hybrid and said inbred seed to obtain (i) $F_1$ hybrid seed and (ii) inbred seed, characterized in that said plant is a cereal plant, said plants are inter-planted at a ratio which provides for pollination of a substantial majority of said female plants and wherein said seed are separated on the basis of a difference which is detectable via the use of near infrared light.

The term "Hybrid" equals "$F_1$ Hybrid". The term "hybrid" equals "$F_1$ hybrid". The term "seed" may be interchanged with the term "grain". The term "Inter-plant" means that the male and female plants are planted in relative close proximity such that upon harvest, the seed will comprise a mixture of the hybrid seed and the inbred seed. Inter-planting will, therefore, prevent the harvesting of the pure hybrid seed per se, since it will not be possible to avoid harvesting the male inbred seed due to the proximity of the male plants within the field containing the females. The male pollinator plants may be planted at specific points within the population of the females, in rows or other patterns within the population of the females. Inter-planting will, however, make it impossible to harvest the field without harvesting both hybrid and inbred seeds mixed in together. The skilled person is generally familiar with the "inter-planting" principle. The term "separation" when applied to seeds equals "sorting".

The male sterile plant for use in the present invention can be generated via numerous techniques well known to the person skilled in the art and as referred to above. In a particular embodiment, the male sterile plant is generated via a Cytoplasmic male sterility (CMS) approach. Such an approach is described in inter alia: (Wilson, J. A., and W. M. Ross. 1961. Cross-breeding in wheat, *Triticum aestivum* L: I. Frequency of the pollen-restoring character in hybrid wheats having *Aegilops ovata* cytoplasm; Crop Sci. 1: 191-193; Wilson, J. A., and W. M. Ross. 1962. Cross-breeding in wheat, *Triticum aestivum* L: II. Hybrid seed set on a cytoplasmic male-sterile winter wheat composite subjected to cross-pollination. Crop Sci. 2: 415-417; Chen. 2003. Improving male fertility restoration of common wheat for *Triticum timopheevii* cytoplasm. Plant Breeding 122, pp 401-404; and Bread Wheat—Improvement and Production 2002 Edited by Curtis, Rajaram and Gomez Macpherson ISBN: 9251048096—In particular the "Hybrid Wheat" section by G. Cisar and D. B. Cooper). The person skilled in the art will recognise that the above general principles of hybrid production are also applicable to the production of hybrid barley. The CMS system for barley has been extensively described by Ahokas et al (Ahokas, H. 1979. Cytoplasmic male sterility in barley. III. Maintenance of sterility and restoration of fertility in the msml cytoplasm. Euphytica 28: 409-419; Ahokas, H. 1980. Cytoplasmic male sterility in barley. VII. Nuclear genes for restoration. Theor. Appl. Genet. 57: 193-202; Ahokas, H. 1982. Cytoplasmic male sterility in barley. XI. The msm2 cytoplasm. Genetics 102: 285-295; Ahokas, H., and E. A. Hockett. 1981. Performance tests of cytoplasmic male-sterile barley at two different latitudes. Crop Sci. 21: 607-611) and this has been used in the production of barley hybrids (Ramage R T (1983) Heterosis and hybrid seed production in barley. In: Frankel R (ed) Heterosis: reappraisal of theory and practice. (Monogr Theor Appl Genet vol 6). Springer, Berlin Heidelberg New York, pp 71-93), which has subsequently been developed into a commercial system.

In a further embodiment the male sterile plant is generated via chemical utilising genetic modification approach such as the system is described further in WO2005/005641.

It should also be borne in mind that the method of the present invention advantageously allows for the male and female parents to be inter-planted without the need for the male fertile donor parent to be removed from the population following pollination of the female parent. This method therefore obviates the need and expense involved in chemically or mechanically removing the males from the population following pollination. Even more advantageously, the methods according to the present invention overcome the problems and expense associated with the bay-planting system as described above. Furthermore, the method of the present invention allows both the hybrid seed and the inbred seed to be utilized commercially.

The term "at least partially male sterile" means that the female parent is capable of being either cross pollinated with pollen from a separate male parent plant or can, under certain conditions self-pollinate. For the production of hybrid plants the female parent will be pollinated via pollen from a separate male parent plant inter-planted with the female.

The skilled person will appreciate that the male plants should be inter-planted with the females in such a way that there is the maximum opportunity for the pollen to be transferred to the females within the field. This will normally involve evenly distributing the male plants throughout the field such that all females are within proximity of a male plant at a distance that would be acknowledged by the skilled man as acceptable to achieve pollination. It is well within the ambit of the skilled person to design the inter-planting field plan based on the size and shape of the field.

The present invention still further provides a method as described above wherein said ratio provides for pollination of a substantial majority of said female plants whilst minimizing the number of self-fertilised male plants thereby maximizing the hybrid seed yield within the total seed yield of said field. In a particular embodiment of the invention said ratio provides for the minimum number of male plants required to achieve pollination of a substantial majority of said female plants thereby maximizing the hybrid seed yield within the total seed yield of said field.

The present invention still further provides a method as described above wherein said female parents are fully male sterile.

The term "fully male sterile" means that the female parent is incapable of self-pollinating and thus can only be cross-pollinated with pollen from a separate male parent plant inter-planted with the female. The term "fully male sterile" may also be interchanged with the term "male-sterile".

The present invention still further provides a method as described above wherein said ratio provides for pollination of at least about 80% of said female plants. In a further embodiment of the invention said ratio provides for pollination of more than 80% of said female plants. In a still further embodiment said ratio provides for pollination of more than 85% of said female plants. In a still further embodiment of the invention said ratio provides for pollination of at least about 90% of said female plants. In a still further embodiment of the invention said ratio provides for pollination of more than 90% of said female plants. In a still further embodiment of the invention said ratio provides for pollination of at least about 95% of said female plants. In a still further embodiment of the invention said ratio provides for pollination of more than 90% of said female plants. In a still further embodiment of the invention said ratio provides for pollination of a substantial majority of said female plants. As mentioned above, it is desirable to maximize the hybrid yield of the field whilst minimizing the number of self-fertilised male plants, thereby maximizing the hybrid seed yield within the total seed yield of said field. This can be demonstrated numerically via Table A below representing a typical hybrid production result:

TABLE A

| (A) % interplant female A line | (B) % interplant male R line | (C) % pollination of female A line | (D) total field yield as % of normal yields | (E) % Female derived F1 seed in harvested field | (F) % Male Seed in harvested field | (G) Hybrid yield as % of normal yields |
|---|---|---|---|---|---|---|
| 100% | 0% | 0% | 0% | 0% | 0% | 0% |
| 99% | 1% | 13% | 14% | 93% | 7% | 13% |
| 98% | 2% | 26% | 27% | 93% | 7% | 25% |
| 97% | 3% | 39% | 41% | 93% | 7% | 38% |
| 96% | 4% | 52% | 54% | 93% | 7% | 50% |
| 95% | 5% | 65% | 67% | 93% | 7% | 62% |
| 94% | 6% | 67% | 69% | 91% | 9% | 63% |
| 93% | 7% | 68% | 70% | 90% | 10% | 63% |
| 92% | 8% | 70% | 72% | 89% | 11% | 64% |
| 91% | 9% | 71% | 74% | 88% | 12% | 65% |
| 90% | 10% | 73% | 75% | 87% | 13% | 65% |
| 89% | 11% | 74% | 77% | 86% | 14% | 66% |
| 88% | 12% | 76% | 78% | 85% | 15% | 66% |
| 87% | 13% | 77% | 80% | 84% | 16% | 67% |
| 86% | 14% | 79% | 82% | 83% | 17% | 68% |
| 85% | 15% | 80% | 83% | 82% | 18% | 68% |
| 84% | 16% | 82% | 84% | 81% | 19% | 68% |
| 83% | 17% | 83% | 86% | 80% | 20% | 69% |
| 82% | 18% | 85% | 87% | 79% | 21% | 69% |
| 81% | 19% | 86% | 89% | 79% | 21% | 70% |
| 80% | 20% | 88% | 90% | 78% | 22% | 70% |
| 79% | 21% | 89% | 91% | 77% | 23% | 70% |
| 78% | 22% | 91% | 93% | 76% | 24% | 71% |
| 77% | 23% | 92% | 94% | 75% | 25% | 71% |
| 76% | 24% | 94% | 95% | 75% | 25% | 71% |
| 75% | 25% | 95% | 96% | 74% | 26% | 71% |
| 74% | 26% | 95% | 96% | 73% | 27% | 70% |
| 73% | 27% | 95% | 97% | 72% | 28% | 70% |
| 72% | 28% | 96% | 97% | 71% | 29% | 69% |
| 71% | 29% | 96% | 97% | 70% | 30% | 68% |
| 70% | 30% | 96% | 97% | 69% | 31% | 67% |
| 69% | 31% | 96% | 97% | 68% | 32% | 66% |
| 68% | 32% | 96% | 98% | 67% | 33% | 66% |
| 67% | 33% | 97% | 98% | 66% | 34% | 65% |
| 66% | 34% | 97% | 98% | 65% | 35% | 64% |
| 65% | 35% | 97% | 98% | 64% | 36% | 63% |
| 64% | 36% | 97% | 98% | 63% | 37% | 62% |
| 63% | 37% | 97% | 98% | 62% | 38% | 61% |
| 62% | 38% | 98% | 99% | 61% | 39% | 61% |
| 61% | 39% | 98% | 99% | 60% | 40% | 60% |
| 60% | 40% | 98% | 99% | 60% | 40% | 59% |
| 59% | 41% | 98% | 99% | 59% | 41% | 58% |
| 58% | 42% | 98% | 99% | 58% | 42% | 57% |
| 57% | 43% | 99% | 99% | 57% | 43% | 56% |
| 56% | 44% | 99% | 99% | 56% | 44% | 55% |
| 55% | 45% | 99% | 99% | 55% | 45% | 54% |
| 54% | 46% | 99% | 100% | 54% | 46% | 54% |
| 53% | 47% | 99% | 100% | 53% | 47% | 53% |

TABLE A-continued

| (A) % interplant female A line | (B) % interplant male R line | (C) % pollination of female A line | (D) total field yield as % of normal yields | (E) % Female derived F1 seed in harvested field | (F) % Male Seed in harvested field | (G) Hybrid yield as % of normal yields |
|---|---|---|---|---|---|---|
| 52% | 48% | 100% | 100% | 52% | 48% | 52% |
| 51% | 49% | 100% | 100% | 51% | 49% | 51% |
| 50% | 50% | 100% | 100% | 50% | 50% | 50% |

It therefore follows that a production field with 25% male component and 75% female component will provide a hybrid yield of 74% and a male self-pollinated yield of 26% of the field. This distribution of male/female provides the highest hybrid yield as a percent of normal fully fertile yields (71%). In accordance with the present invention this population can then be sorted into the respective 74% hybrid seed and 26% male inbred seed allowing the sale of pure hybrid seed and the use of male seed in further production or sale into well-known grain channels. The person skilled in the art is capable of selecting the appropriate ratio of males:females to maximise the hybrid yield within the total seed yield of the field. The skilled person will also appreciate that each individual male/female genetic combination may have its own optimum percentage mix due to differential seed setting ability associated with genetic control of female receptivity and male pollen potential.

It is also an aspect of the present invention that the separation can be undertaken rapidly. In a particular embodiment the seeds can be separated at a rate of about 10 imperial tonnes (of total seed) per hour. In a still further embodiment the seeds can be separated at a rate of about 30 imperial tonnes per hour. In a still further embodiment the seeds can be separated at a rate in excess of 55 imperial tonnes per hour. Throughout this specification the term "tonnes" is expressed in "imperial tonnes".

In a still further aspect of the invention there is provided a harvesting machine for harvesting and separating substantially pure $F_1$ hybrid cereal seed and substantially pure inbred cereal seed which machine comprises a means for harvesting cereal seed from mature cereal plants and a means for separating said seed on the basis of a difference between said hybrid and said inbred to obtain (i) $F_1$ hybrid cereal seed and (ii) inbred cereal seed wherein said seed are separated on the basis of a difference which is detectable via the use of near infrared light. In a particular embodiment of the invention said cereal seed are barley seed.

In a still further aspect of the invention there is provided the use of a seed separating device in the separation of hybrid cereal seed and inbred cereal seed wherein said separation is on the basis of a difference between said hybrid and said inbred wherein said difference is detectable via the use of near infrared light. In a particular embodiment of said use said cereal seed are barley seed. In an alternative embodiment of said use said cereal seed are wheat seed.

The methods described within this specification may be applicable to other cereal plants where it is advantageous to separate the hybrid seed from the inbred parental seed. In particular, the methods described above may be utilised to generate substantially pure hybrid barley seed and substantially pure inbred barley seed. Furthermore, the methods may be utilised to generate substantially pure hybrid wheat seed and substantially pure inbred wheat seed. Furthermore, the methods may be utilised to generate substantially pure hybrid rye seed and substantially pure inbred rye seed. Furthermore, the methods may be utilised to generate substantially pure hybrid triticale seed and substantially pure inbred triticale seed.

In a still further aspect of the invention there is provided a method, a machine, and a use as described throughout this specification wherein the term "barley" is substituted for "wheat". In a still further aspect of the invention there is provided a method, a machine, and a use as described throughout this specification wherein the term "barley" is substituted for "rye". In a still further aspect of the invention there is provided a method, a machine, and a use as described throughout this specification wherein the term "barley" is substituted for "triticale".

The invention will now be demonstrated via the following non-limiting example:

EXAMPLE

Experimental Protocol for Single Seed NIR Measurements

There are many optical sorting technologies available on the market today to sort on a single seed basis. Each seed is measured and its spectral features compared with predetermined values. Based on this comparison, the seed can be classified and sorted into different fractions with each fraction showing a different seed quality. The following method has been developed to sort hybrid cereals seeds from inbred male lines using near-infrared spectroscopy. Seven (7) barley breeding samples (Table 1 & 2) were analyzed by NIR, in both reflectance (NIRS) & transmission mode (NITS), and the resulting spectral data was used to develop a classification model. The results showed that spectra between individual intact seeds were not significantly different when normalized spectra were used; these measurements could be averaged yielding one spectrum per variety. However, for the purposes of this study, the classification used a single spectrum per seed, not the average spectrum per variety. Spectral regions were found where hybrid & male inbred seeds differed in normalized signal. For the chosen sample set, distributions partially overlapped, however, it is possible to develop a mathematical model to discriminate between the different classes. An efficient sorting method can be used to ensure the harvested hybrid seed meets tolerance levels for inbred "contamination"—i.e. where the number of inbred seed present in a population of hybrid seed is limited to a particular percentage.

TABLE 1

Reflectance Measurements: Sample set 1

| Variety | Type | No. of seeds measured | Total sample size |
|---|---|---|---|
| RE 07 | Male Inbred line | 12 | 72 |
| RE 11 | | 24 | |
| RE 15 | | 24 | |
| RE 18 | | 12 | |

TABLE 1-continued

Reflectance Measurements: Sample set 1

| Variety | Type | No. of seeds measured | Total sample size |
|---|---|---|---|
| Fm 37-97 | Female Inbred Line | 48 | 48 |
| 10-1500 | Hybrids | 48 | 108 |
| 10-1517 | | 60 | |

TABLE 2

Transmission Measurements: Sample set 2

| Variety | Type | No. of seeds measured | Total sample size |
|---|---|---|---|
| RE 11 | Male Inbred line | 12 | 24 |
| RE 15 | | 12 | |
| Fm 37-97 | Female Inbred Line | 24 | 24 |
| 10-1500 | Hybrids | 11 | 23 |
| 10-1517 | | 12 | |

General Procedure: NIR Instrument & Spectra Acquisition

The instrument consists of an NIR spectrometer of type Bruker MPA Multi Purpose FT-NIR Analyzer (www.bruker-optics.com/ft-nir).

TABLE 3

Technical specifications:

| Detector type | Reflectance PbS (Lead sulphide) | Transmission InGaAs (Indium gallium arsenide) |
|---|---|---|
| Wave number range | 12500-3600 cm−1 | 12500-5800 cm−1 |
| Wavelength range | 800-2780 nm | 800-1720 nm |
| Number of scans | 32 | 32 |
| Spectra resolution | 4 cm−1 | 4 cm−1 |

In reflectance mode, individual seeds are illuminated by light of a pre-defined spectrum and the spectral features of the reflected light are measured. The light is partly absorbed in different wavelength intervals depending on different seed properties. The light that comes back from the seed is captured by a detector and analyzed. Seeds were measured one by one by hand. This means that each individual seed was manually positioned on a small metal plate centered above a 2 mm diameter hole in the centre of the plate. The plate was positioned 2 cm above the glass window of the instrument and the light was focused to illuminate a small spot on the seed. Any light that reflected back on an integrating sphere was recorded and the resulting spectrum was captured by computer and stored on hard disk. In transmission mode the detector was positioned opposite to the light source to measure the absorbance of light through individual seeds.

At the start of each experiment the instrument was allowed to warm to its operating conditions for at least one (1) hour and then a background spectrum was recorded using a gold surface. A new background spectrum was recorded after every 12 samples. Each seed was scanned thirty-two (32) times and an average spectrum recorded containing 2307 (reflectance) or 1737 (transmission) data points. Since the measurements are on a single seed basis each spectrum was given a unique code that belonged to the measured seed. For identification purposes seeds were then stored in one of the wells of a 96 well plate. We found that spectra between individual seeds of the same variety were not significantly different when normalized spectra were used; these measurements could be averaged yielding one spectrum per variety.

Data Treatment

Spectral data were loaded in R (statistical program, cran.r-project.org), each with a unique code and each belonging to one of three classes: male, female or hybrid. The spectral data of the different inbred male seeds were combined in the classification model to provide a data set corresponding to generic male seed. Likewise the spectral data from the two hybrid samples were combined. PLS-DA (Partial Least Squares-Discriminant Analysis) was used to discriminate between the different classes. Sixty-seven percent (67) of the total samples in each class (Table 1 & 2) were chosen randomly for the calibration set and the remaining thirty-three (33) percent were used for the validation set. This process was repeated ten (10) times with different validation and training (calibration) sets. To optimize the classification different regions of the spectra were investigated and different pre-treatments applied such as: first and second derivative; with and without multiplicative scattering correction. Finally, the first derivative and MSC treatment afforded the prediction tables shown in Tables 4 & 5.

Results

Spectral regions were found where hybrid & male inbred seeds differed in normalized signal. For the chosen sample set, and given that samples were grouped into classes, distributions partially overlap. However, it is possible to develop a mathematical model to discriminate between the different classes. The results are presented in Tables 4 & 5 and show the average classification accuracy, after ten (10) repeats, of the mathematical model to correctly predict and assign the validation set against the calibration set for each seed class.

TABLE 4

Prediction results in reflectance mode: Average percentage of individual seeds correctly classified in the validation set

| | | True | | |
|---|---|---|---|---|
| | | Hybrid | Female | Male |
| Predicted by NIR | Hybrid | 85 | 14 | 5 |
| | Female | 7 | 85 | 1 |
| | Male | 8 | 1 | 94 |

TABLE 5

Prediction results in transmission mode: Average percentage of individual seeds correctly classified in the validation set

| | | True | | |
|---|---|---|---|---|
| | | Hybrid | Female | Male |
| Predicted by NIR | Hybrid | 74 | 22 | 11 |
| | Female | 20 | 78 | 0 |
| | Male | 7 | 0 | 89 |

In conclusion, the NIRS & NITS calibration models developed in this example permit the non-destructive single seed sorting of hybrid barley samples from their respective male inbreds.

The invention claimed is:

1. A method for separating inbred seed from a mixed population of inbred and hybrid seed characterized in that the method comprises the following steps:
   (a) providing a mixed population of inbred and hybrid seed, which population is generated by:
      (i) Inter-planting a population of parent plants within a field wherein said population contains male and female parents; and
      (ii) Providing for self-fertilization of said male and cross-fertilization of said female; and
      (iii) Harvesting the resulting fertilized seed to provide said mixed population; and
   (b) Subjecting said seed to a device which separates said mixed population into:
      (i) A population of substantially inbred seed; and
      (ii) A population of substantially hybrid seed wherein said seed is wheat or barley seed and said device separates said seed on the basis of a difference which is detectable via the use of near infrared light.

2. A method according to claim 1, wherein said device separates the seed such that the resulting population of separated substantially hybrid seed comprises no more than about 5% inbred seed.

3. A method according to claim 1 wherein said device utilises an algorithm to differentiate the near infrared spectral data obtained of said inbred and said hybrid seed which then allows the seed to be sorted on the basis of said spectral data.

4. A method according to claim 1 wherein said difference is a genotypic difference.

5. A method according to claim 1 wherein said difference relates to an amount of a compound selected from: glucose; xylose; mannose; galactose; arabinose; or a combination thereof, in the seed.

* * * * *